(12) United States Patent
Zimmermann (10) Patent No.: US 8,355,561 B2
(45) Date of Patent: Jan. 15, 2013

(54) METHOD FOR SCREENING OF MULTI-JUNCTION SOLAR CELLS

(75) Inventor: Claus Zimmermann, Munich (DE)

(73) Assignee: Astrium GmbH, Taufkirchen (DE)

( * ) Notice: Subject to any disclaimer, the term of this patent is extended or adjusted under 35 U.S.C. 154(b) by 88 days.

(21) Appl. No.: 13/089,031

(22) Filed: Apr. 18, 2011

(65) Prior Publication Data

US 2011/0255772 A1   Oct. 20, 2011

(30) Foreign Application Priority Data

Apr. 19, 2010   (EP) .................... 10004129

(51) Int. Cl.
*G06K 9/00* (2006.01)
(52) U.S. Cl. ..................... 382/145; 382/273
(58) Field of Classification Search .......... None
See application file for complete search history.

(56) References Cited

U.S. PATENT DOCUMENTS

| 2010/0034455 A1* | 2/2010 | Harada et al. ............ 382/141 |
| 2010/0150428 A1 | 6/2010 | Andreev et al. |
| 2010/0266196 A1* | 10/2010 | Kasahara et al. ......... 382/149 |
| 2011/0025839 A1* | 2/2011 | Trupke et al. ............ 348/87 |

FOREIGN PATENT DOCUMENTS

| DE | 10 2007 007 140 A1 | 8/2008 |
| EP | 1 416 288 A1 | 5/2004 |

OTHER PUBLICATIONS

Zimmermann, C., "Utilizing lateral current spreading in multijunction solar cells: An alternative approach to detecting mechanical defects", Journal of Applied Physics, American Institute of Physics, New York, US LNKD-DOI: 10.1063/1.2216868, vol. 100, No. 2, Jul. 26, 2006, pp. 23714-1-23714-8, XP012089468.
Zimmermann, C. G., "Performance Mapping of Multijunction Solar Cells Based on Electroluminescence", IEEE Electron Device Letters, vol. 30, No. 8, Aug. 2009, pp. 825-827, XP011263984.
Zimmermann, Claus G, "Assessing the In-Orbit Impact of Cell Cracks—An Electroluminescence Study of Crack Propagation", May 1, 2006, Photovoltaic Energy Conversion, Conference Record of the 2006 IEEE 4th World Conference on, IEEE, PI, pp. 1850-1853, XP031007691.
European Search Report dated Sep. 13, 2010 (eleven (11) pages).

* cited by examiner

*Primary Examiner* — Manav Seth
(74) *Attorney, Agent, or Firm* — Crowell & Moring LLP (57) ABSTRACT

A method for screening of multi-junction solar cells to be operated in a high sun intensity and high temperature (HIHT) environment. An electroluminescence image of a homogeneous pn-junction at a predefined bias current is acquired for each of the solar cells. The spatial intensity distribution in the electroluminescence image is analyzed to determine whether there are local intensity variations that possibly dissipate power in a HIHT environment. The solar cells are sorted such that solar cells having no local intensity variations in their electroluminescence image are put into a first group and solar cells having at least one local intensity variation in their electroluminescence image are put into a second group cells for further screening. The solar cells of the first group are suitable for a HIHT environment and solar cells of the second group are assumed to be potentially critical in a HIHT environment.

13 Claims, 8 Drawing Sheets

METHOD FOR SCREENING OF MULTI-JUNCTION SOLAR CELLS

CROSS REFERENCE TO RELATED APPLICATIONS

This application claims priority under 35 U.S.C. §119 to European Patent Application No. 10 004 129.2, filed Apr. 19, 2010, the entire disclosure of which is herein expressly incorporated by reference.

BACKGROUND AND SUMMARY OF THE INVENTION

The invention relates to a method for screening of multi-junction solar cells used in high intensity and high temperature environments, each of the solar cells comprising at least two pn-junctions stacked on top of each other.

Solar cells are large area devices characterized by the fact that their lateral dimensions usually in the range of a few centimeters and are orders of magnitude larger than their thickness, which is in the range of some 10 to 100 micrometers. Advanced solar cells very often feature a multi-junction layout in which several pn-junctions are stacked on top of one another. The bandgaps of the individual junctions decrease from top to bottom. Therefore, each junction is sensitive to only part of the spectrum, which greatly reduces thermalization losses and results in higher efficiencies.

Figure 1:
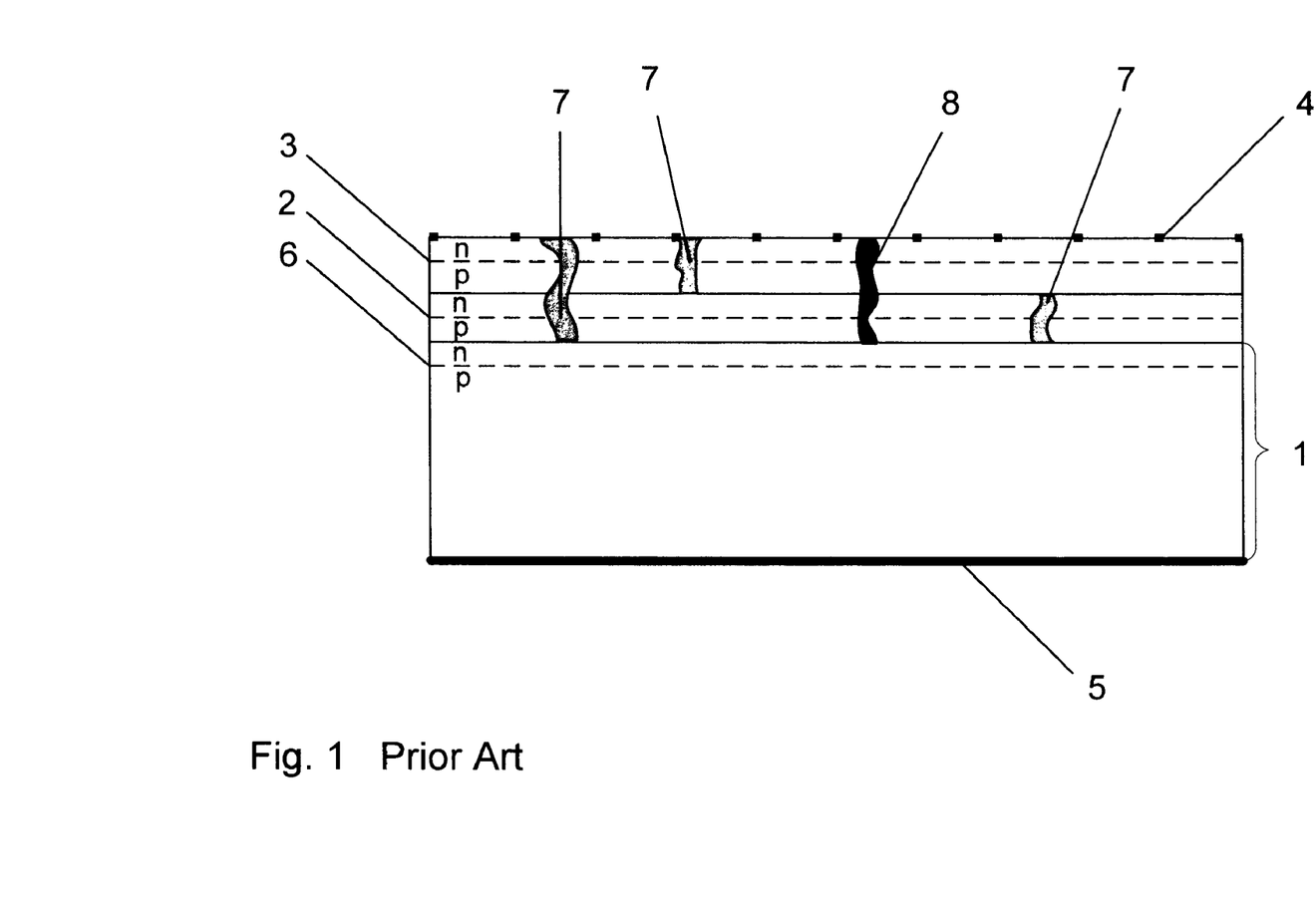
FIG. 1 shows a triple-junction solar cell known from prior art.

A typical example is III-V triple junction solar cells as illustrated in cross section in FIG. 1. A single crystalline Germanium (Ge)-wafer 1, typically around 100 micrometers thick, is used as a growth substrate. By metal organic vapour phase expitaxy (MOVPE), the GaAs pn-junction 2 followed by a GaInP$_2$ junction 3 as well as several support layers (such as tunnel diodes, back surface fields, etc.) are grown epitaxially on this substrate. With a front metallization 4 and a rear side metallization 5 as well as an activation of the Ge-wafer itself by diffusion (depicted with reference numeral 6) the configuration shown in FIG. 1 electrically resembles a series connection of three solar cells. The order of the pn doping (n on top) is not relevant.

Due to the large lateral dimensions of the solar cells, in practice very difficult to obtain MOVPE grown layers completely free of areas where the epitaxial growth is distorted. These areas are called growth defects. While a lot of these defects have a negligible electrical impact (cf. reference numeral 7) some of them denoted with reference numeral 8 can act as an ohmic or diode like shunt. In this context, a diode like shunt is a growth defect with a lower open circuit voltage (Voc) than the remaining cell area. These shunts dissipate power produced by the surrounding undisturbed cell area. In contrast, the growth substrate 6 can be assumed to be free of intrinsic defects.

A spatially resolved electrical characterization technique is necessary in order to detect these shunts in a given solar cell.

Figure 2:
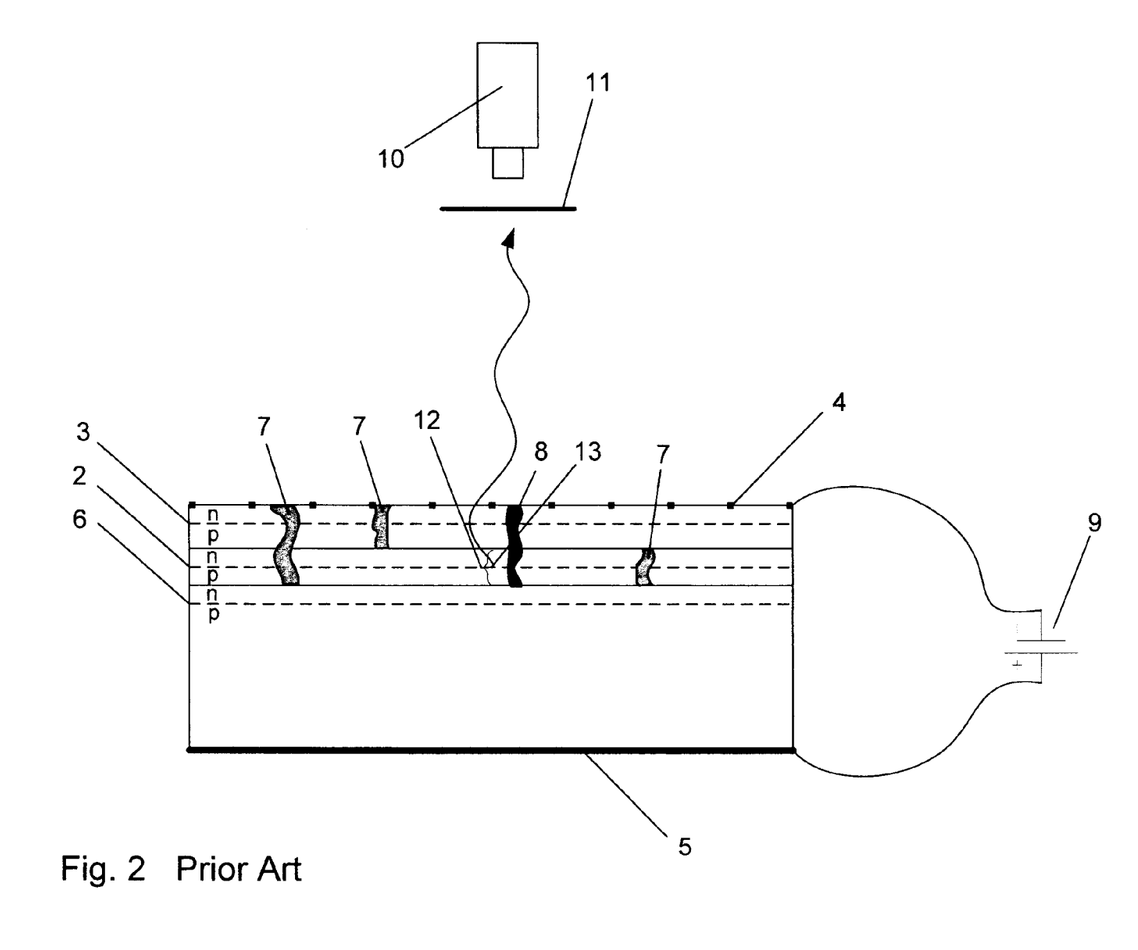
FIG. 2 shows a measurement arrangement to locally characterize the solar cell according to FIG. 1 by electroluminescence imaging.

A known technique to characterize a solar cell locally is electroluminescence imaging. This procedure is illustrated in FIG. 2. The solar cell is forward biased with an external power supply 9 at a particular current 1. The electroluminescence radiation emitted by a given junction, e.g. pn-junction 2, is recorded with an appropriate detector, for example a Si or InGaAs CCD chip 10 in combination with appropriate filters 11. The emitted electroluminescence intensity is exponentially dependent on the local junction voltage V (cf. reference numeral 12) at any position xy (cf. reference numeral 13) on the solar cell. Due to this very sensitive voltage dependence, the location of growth defects can be easily identified. Even defects in junctions not imaged directly, e.g. pn-junction 3, appear with an inverse contrast in the imaged junction due to the electrical series connection. A decrease in the local voltage in one junction, for example, automatically leads to a higher voltage at the remaining junctions because the external voltage V between the front metallization 4 and the rear side metallization 5 is constant everywhere when series resistance effects are neglected. However, the defects cannot be classified according to their electrical impact.

Figure 3:
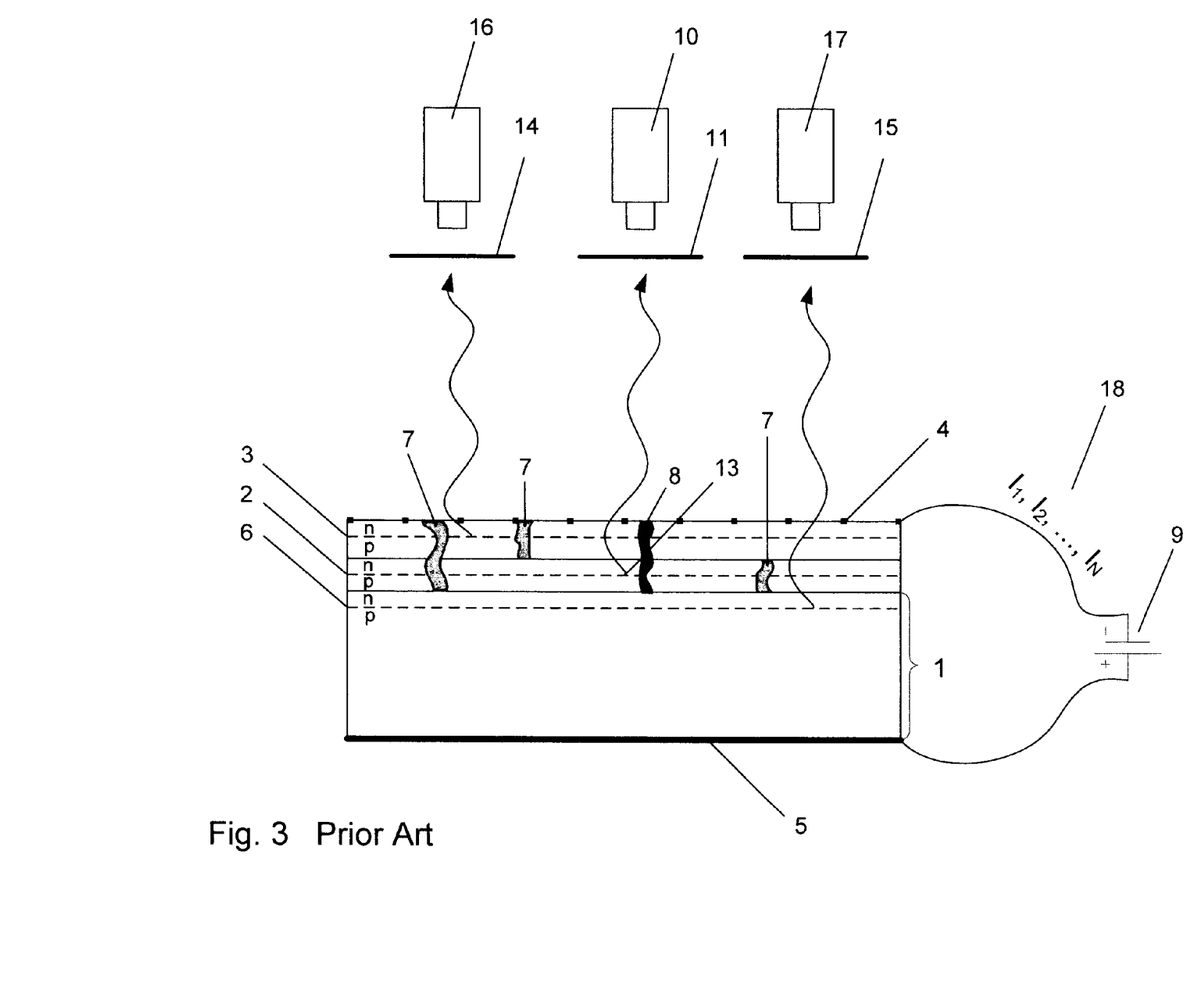
FIG. 3 shows an improved measurement arrangement according to the prior art.

A measurement concept based on electroluminescence imaging for III-V triple junction solar cells that allows classifying defects according to their electrical impact is disclosed in the article [C. G. Zimmermann, "Performance Mapping of Multijunction Solar Cells Based on Electroluminescence", IEEE ELECTRON DEVICE LETTERS, Vol. 30, No.8,August 2009, , pages 825-827]. With this procedure the electroluminescence radiation is recorded in a spatially resolved manner by planar detectors with appropriate filters. This is schematically illustrated in FIG. 3 showing three detectors 10, 16, 17 and assigned filters 11, 14, 15. All detectors image the entire area of the solar cell. For the sake of simplicity, in FIG. 3 the detectors are illustrated parallel to each other. As an alternative, it would be possible to move the solar cell from one detector 10, 16 to the next detector 16, 17. It is also feasible to use a common detector for several subcells, i.e. the amount of pn-junctions 2, 3, 6 stacked on top of each other, and select the emission of one particular subcell by interchangeable filters.

In addition, the solar cell is forward biased at a range of different injection currents $I_1, I_2, \ldots, I_N$ (cf. reference numeral 18) up to or beyond the short circuit current of the solar cell. As a result, the combined voltage of all three pn-junctions can be inferred in a spatially resolved manner from the combined electroluminescence intensities of all junctions. In order to be able to calculate the local diode properties of an equivalent single junction cell, the local current density also has to be known. Therefore the fact that the bottom cell pn-junction 6 is not grown by MOVPE but is based on a single crystalline Ge-wafer is used. Its electroluminescence properties and diode properties can be assumed to be spatially homogeneous. Under these circumstances the measured electroluminescence intensity of the bottom cell follows a power law dependence on the local current and the bottom cell electroluminescence images serve as a map of the current distribution. Within this framework, the local diode properties of the cell can be calculated and from them the amount of current Iop, i.e. operation current, produced or dissipated at any position xy (cf. reference numeral 13) on the solar cell at a given operating condition is inferred. Because it is necessary to acquire images with high dynamic resolution of all junctions at a range of injection currents, the data acquisition time is in the range of several minutes, typically 10 to 15 minutes.

Since several thousand solar cells are required for the solar array, this more precise method is too costly and time consuming to screen each of the solar cells in this way. Alternatively, a direct screening of the cells by exposing them to their intended high temperature high intensity environment followed by an electrical performance measurement poses the risk of introducing artificial damage, e.g. if the screening is performed in air.

Exemplary embodiments of the present invention provide a more effective method for screening of multi-junction solar cells that are operated in space.

According to the invention, a method for screening of multi-junction solar cells to be operated in a high sun intensity and high temperature (HIHT) environment is provided, wherein each of the solar cells comprises at least two pn-junctions stacked on top of each other and wherein one of the pn-junctions is a homogeneous pn-junction assumed to be free of intrinsic defects. The method comprises the steps of providing a number of solar cells to be screened for usability in a HIHT environment; for each solar cell of the number of solar cells, acquiring an electroluminescence (EL) image of the homogeneous pn-junction at a predefined bias current, and analyzing the spatial intensity distribution in the electroluminescence image to determine whether there are local intensity variations that possibly dissipate power in a HIHT environment; sorting the solar cells wherein solar cells having no local intensity variations in their electroluminescence image are put into a first group of solar cells and solar cells having at least one local intensity variation in their electroluminescence image are put into a second group of solar cells for further screening wherein solar cells of the first group are suitable for HIHT environment and solar cells of the second group are assumed to be potentially critical in a HIHT environment.

The method of the invention is based on the consideration that under normal operation conditions in space with temperatures of around 50° C. and an irradiance of one sun as detailed in the AM0 spectrum [*Solar Constant and Air Mass Zero Solar Spectral Irradiance Tables*, (American Society for Testing and Materials, Philadelphia, 1992), Vol. ASTM-E 490-73a.], local growth defects are of no concern. In contrast, in more extreme environments, characterized by higher sun intensities and higher temperatures (HIHT environment), solar cells may be destroyed electrically by local overheating, i.e. local hotspots. An HIHT environment is characterized, for example, by temperatures of around 250° C. and five times the AM0 spectrum. These environmental parameters are typical for space missions to the inner planets of the solar system, e.g. to Mercury. It was discovered that all solar cells that failed had local areas where current was dissipated. Under the above mentioned operating conditions, the locally dissipated current results in a local temperature increase. This in turn lowers the relevant parameters of a defect, e.g. the open circuit voltage Voc even more with an even bigger current dissipation. Hence, the solar cell is eventually destroyed in a positive feedback loop. For solar arrays, it is critical to exclude any solar cell that is susceptible in this way in a HIHT environment, in particular because subsets of solar cells are interconnected in series (so-called cell string) to reach the desired bus voltage. Therefore, the loss of any solar cell can result in the loss of the entire string. In addition, the thermal effect of hot spots can result in an insulation failure of one solar array with even more serious consequences.

Based on this knowledge, the method for screening of multi-junction solar cells according to the invention uses a simplified screening process that in a first step just separates those solar cells where at least one local intensity variation in their electroluminescence image of the homogeneous pn junction has been found from those where no such local intensity variation occurs. It has been found that solar cells having no such local intensity variation in their electroluminescence image are not critical for use in a HIHT environment because no power is dissipated locally. The other solar cells might be critical and will therefore be subject to a more detailed screening process. As a result, the screening of a huge amount of solar cells can be carried out in shorter time and without the risk of introducing artificial damage compared to an exposition to a simulated HIHT environment as set out in the prior art. The screening method of the invention is therefore cost efficient and time saving.

According to an aspect, the step of analyzing the spatial intensity distribution in the electroluminescence image of the homogeneous pn junction comprises the steps of calculating of an average intensity $\Phi_{av}$ of the entire electroluminescence image or a sub-area thereof and calculating the standard deviation $\sigma$; comparing, for each pixel xy of the electroluminescence image, whether the intensity $\Phi_{xy}$ in this pixel is larger than a threshold intensity $\Phi_{th}$, wherein $\Phi_{th}=(\Phi_{av}+n\sigma)$, with n being a predefined constant; and assigning those pixel xy to form a local intensity variation where the intensity $\Phi_{xy}$ is larger than a threshold intensity $\Phi_{th}$ and that are adjacent to each other. It has been found sufficient that n=6 for a triple junction solar cell which are preferred to be used in space due to their high efficiencies.

According to a further aspect, the step of analyzing the spatial intensity distribution in the electroluminescence image is executed by an image processing system.

According to a further aspect, the homogeneous pn-junction is a single crystalline wafer, particularly a Germanium (Ge)-wafer, on which the at least one further pn-junction is grown. The growth of the at least one further pn-junction may be made with metal organic vapour phase epitaxy (MOVPE).

According to a further aspect, during the screening process solar cells are placed on a temperature controlled plate that is heated to a predefined temperature. In principle, the temperature chosen during the screening process is not relevant. However, room temperature during the screening process is most straight forward.

According to a further aspect, an electroluminescence image is acquired with a detector having a resolution of around 2000 pixel/cm$^2$ and/or having a dynamic resolution of about 1:10000.

According to a further aspect, a set of filters is used to block electroluminescence radiations emitted by other pn-junctions than the homogeneous pn-junction. As a result, only the electroluminescence radiation emitted by the homogeneous pn-junction is detected and processed. This allows acquisition of an electroluminescence image of only the homogeneous pn-junction that is a measure of the local current density. When considering the local intensity variations in the spatial intensity, shunts in the at least one further pn-junction can be detected. Due to the electrical series connection of the sub-cells, i.e. the amount of pn-junctions, they affect the current distribution in all layers.

According to a further aspect, the predefined bias current is a forward current close to the short circuit current of the solar cell such that the solar cell emits sufficient electroluminescence radiation for acquiring the electroluminescence image of the homogeneous pn-junction of the solar cell and that it is not damaged by the bias current.

According to a further aspect, the screening method further comprises the step of screening the solar cells of the second group of solar cells. It further comprises the steps of acquiring an electroluminescence image of all pn-junctions of a respective solar cell and a range of predefined bias currents; for each solar cell of the solar cells of the second group, creating a spatial current distribution map of the current Iop produced by the solar cell at a given cell operating voltage, and identifying pixels xy of a group of adjacent pixels xy with a lowest current value; and sorting those of the solar cells into a third group of solar cells that are not suitable for a HIHT environment based on the lowest current value.

This second more detailed screening step considers the electroluminescence radiation of all pn-junctions of the screened solar cell. By analyzing the lowest current value of pixels or a group of adjacent pixels it is possible to make a decision whether or not the screened solar cell is suitable for a HIHT environment.

According to a further aspect, the step of identifying pixels xy with a lowest current value comprises the step of determining whether or not the lowest current value is negative. When the lowest current value is not negative, no current is dissipated and the solar cell is assorted to a fourth group of solar cells that are suitable for HIHT environment. In contrast, when the lowest current value is negative the second screening step comprises the steps of selecting a subset of solar cells covering the entire spread of negative Iop values; exposing all solar cells of the subset to a simulated HIHT environment; determining solar cells with degraded electrical performance; determining a threshold current being negative above which no electrical degradation occurs; and sorting solar cells with an operating current Iop smaller than a threshold current Ith (Iop<Ith) into the third group and assorting solar cell with Iop>Ith into the fourth group. After having carried out this last step of the screening method the screening process is finished because each of the solar cells is reliably classified as being suitable for a HIHT environment.

Other objects, advantages and novel features of the present invention will become apparent from the following detailed description of one or more preferred embodiments when considered in conjunction with the accompanying drawings.

BRIEF DESCRIPTION OF THE DRAWINGS

The invention will be described in more detail with reference to the accompanying figures.

DETAILED DESCRIPTION OF THE DRAWINGS

The screening process of multi-junction solar cells according to the invention will be described by reference to a triple junction solar cell which has already been described in detail with reference to FIG. 1. However, it is to be understood that the invention is not limited to a triple-junction solar cell.

A single crystalline Ge-wafer 1 of a thickness of around 100 micrometers is used as a growth substrate. By metal organic vapour phase epitaxy (MOVPE) a GaAs pn-junction 2 followed by a GaInP$_2$ pn-junction 3 as well as several support layers (such as tunnel diodes, back surface fields, etc.) are grown epitaxially on this substrate. A front metallization 4 is provided on the front of the solar cell. Furthermore, a rear side metallization 5 is provided on the backside of the solar cells. The Ge-wafer itself is activated by diffusion depicted with reference numeral 6. The configuration resembles electrically a series connection of three solar cells.

As already described, due to the large lateral dimensions of solar cells it is in practice very difficult to obtain MOVPE grown layers completely free of areas where the expitaxial growth is distorted. These areas are growth defects and depicted with reference numerals 7 and 8. While a lot of these defects have negligible electrical impacts, some of them can act as an ohmic or diode like shunt.

In order to determine whether a screened triple-junction solar cell can be operated in a high sun intensity and a high temperature (HIHT) environment characterized, for example, by temperatures of around 250° C. and five times the AM0 spectrum, one electroluminescence image of the homogeneous pn-junction 6 of the solar cell is acquired at a predefined bias current Isc. The current Isc preferably is on the order of the short circuit current of the solar cell.

Figure 4:
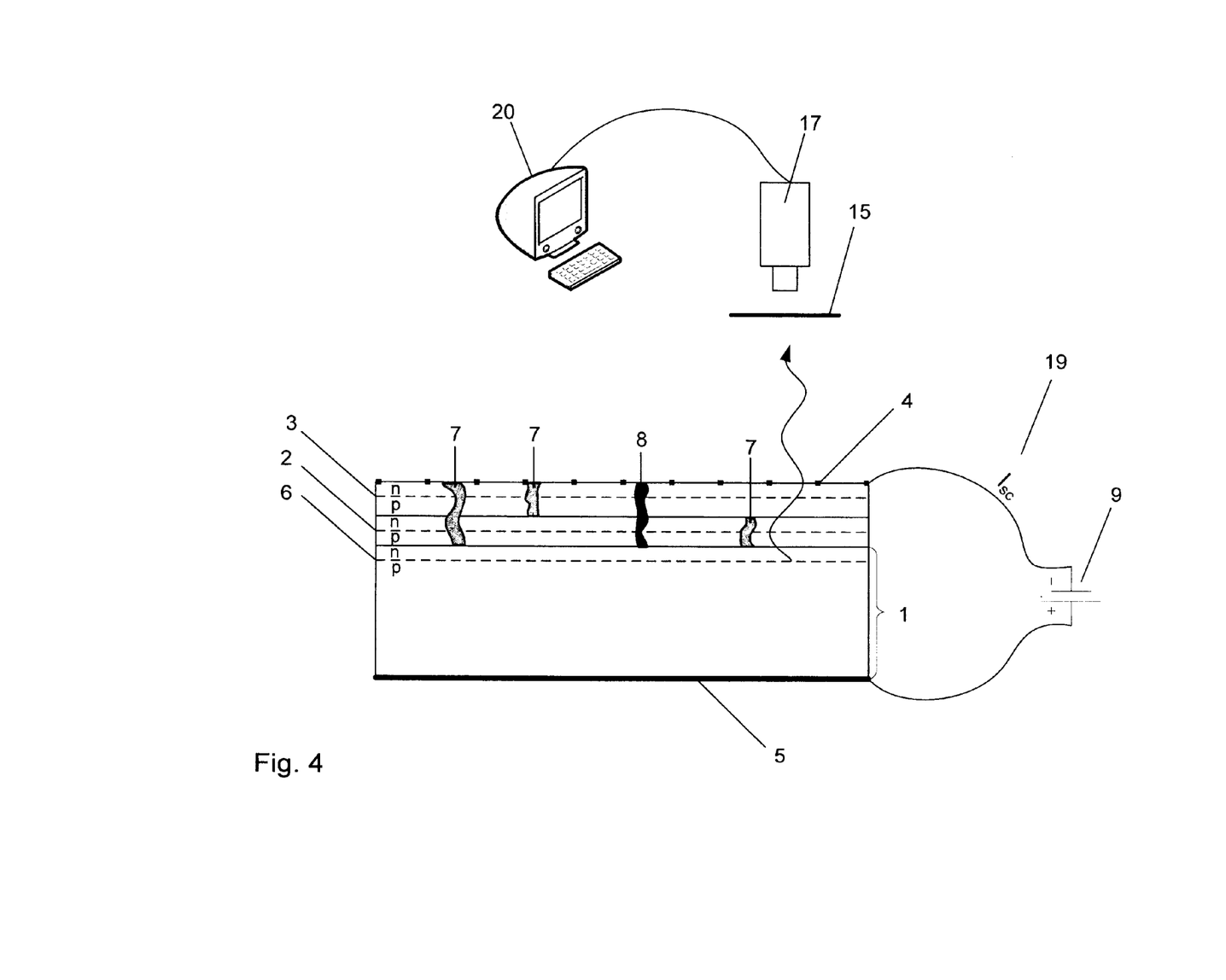
FIG. 4 shows a screening process based on electroluminescence imaging according to the invention.

FIG. 4 shows a basic arrangement for screening a multiplicity of triple-junction solar cells according to the invention. A detector 17, e.g. a CCD-chip, acquires the electroluminescence image of the homogeneous pn-junction 6 of the solar cell. The detector 17 is coupled to a computer 20 for analyzing each of the electroluminescence images and for the determination of whether the solar cell can be used in a HIHT environment without further tests or if further screening is necessary. To ensure that only electroluminescence radiation of the homogeneous pn-junction 6 will be recorded by the detector 17, an appropriate filter 15 is provided in front of it.

Figure 5:
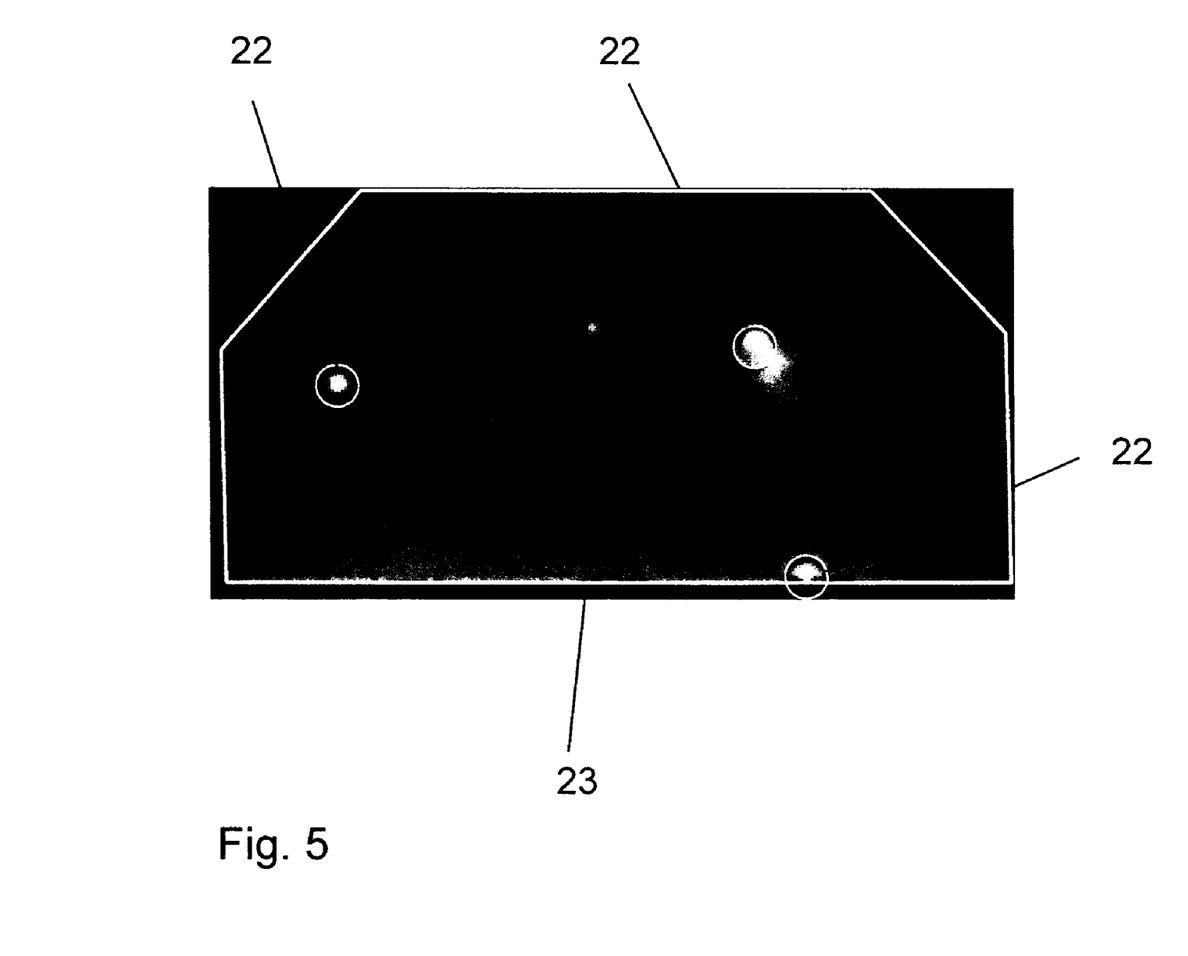
FIG. 5 shows an electroluminescence image of a homogeneous pn-junction of a multi-junction solar cell.

If the analysis of an electroluminescence image, which is in essence a map of a local current density, shows large local intensity variations (so-called bright spots), current could dissipate when the cell is operated in a HIHT environment. Such bright spots or local intensity variations are shown in FIG. 5. FIG. 5 illustrates an electroluminescence image of a subarea 23 of the bottom cell, i.e. the pn-junction 6, of a triple junction solar cell. The local intensity variations are depicted with reference numeral 22.

Solar cells, typically the large majority, that do not have local intensity variations are uncritical in a HIHT environment. With the assistance of the computer 20, an automatic analyzation of each electroluminescence image will be performed to determine whether or not a solar cell is HIHT critical.

A local intensity variation or bright spot 22 is characterized in quantitative terms by the fact that its maximum electroluminescence intensity is above a certain threshold $\Phi th$ determined by the average intensity $\Phi av$ of the entire image or a subarea 23 thereof and the standard deviation $\sigma$:

$$\Phi th = \Phi av + n\sigma.$$

n=6 is applicable for solar cells based on a Ge-wafer. n=6 can also be seen as an appropriate value for other cell technologies.

In a second, optional screening step, all solar cells that were identified to possibly be susceptible to HIHT damage are subjected to a quantitative complete characterization and sorted based on a predetermined threshold for the dissipated current. The threshold is determined based on screening tests where a small number of cells are subjected to the simulated environmental loads, i.e. the HIHT environment in space. The screening process therefore can be experimentally adapted to any cell technology and any given HIHT environment.

Figure 6:
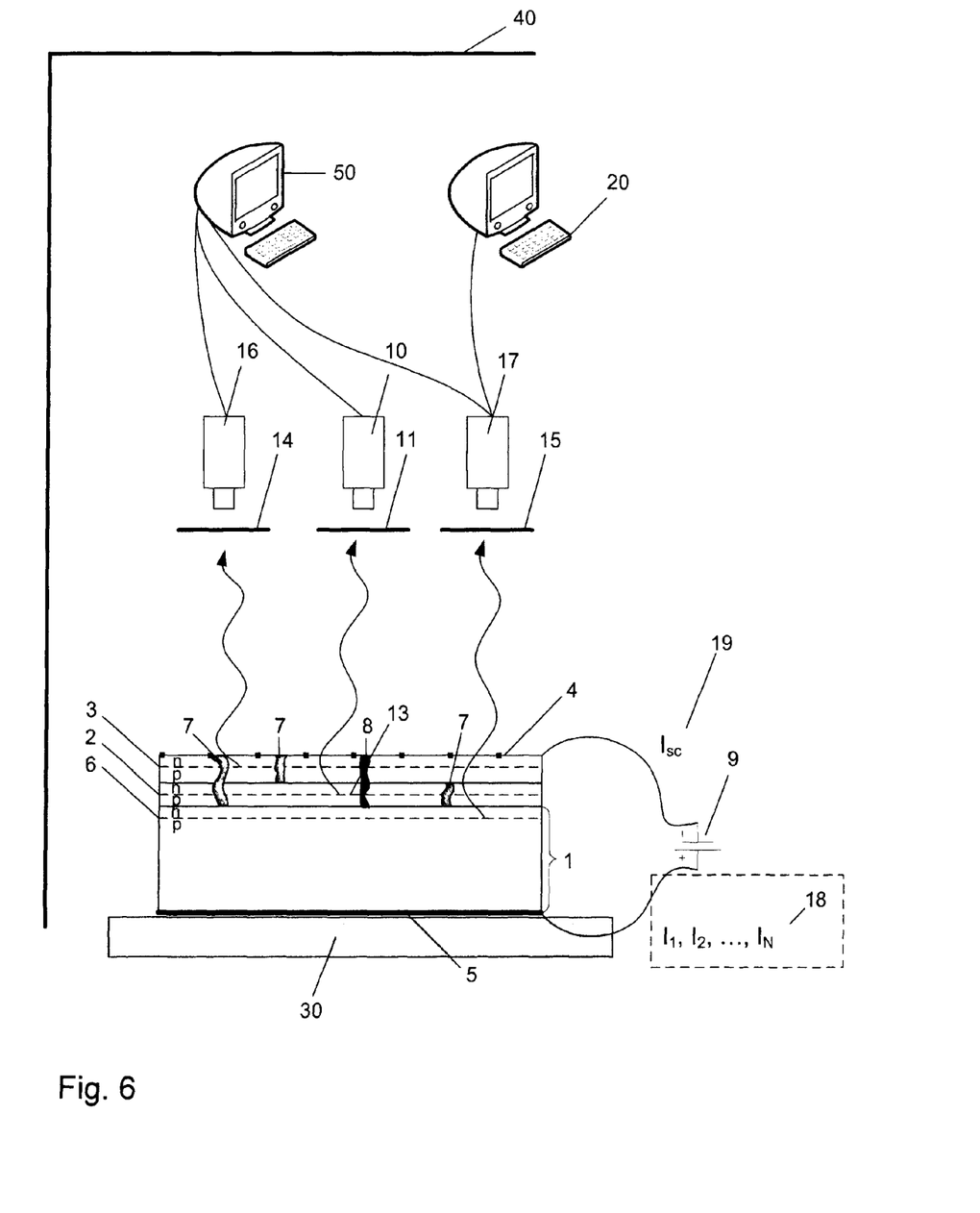
FIG. 6 shows a further measurement arrangement for screening of multi-junction solar cells according to their sensitivity to high sun intensity and high temperature (HIHT) environment.

FIG. 6 shows the screening arrangement to carry out the aforementioned optional second screening step. In addition to the arrangement of FIG. 4, it comprises two more detectors 16, 10 and appropriate filters 14, 11 to additionally select the emission of the particular pn-junction 2 and 3, respectively.

All of the detectors 10, 16, 17 are connected to a further computer 50. In the example shown three detectors 10, 16, 17 corresponding to the number of pn-junctions of the multi-junction solar cell are illustrated. It should be understood that the amount of detectors has to correspond to the number of pn-junctions in principle. This is because the method of the invention can be applied to multi-junction solar cells having a freely chosen number of pn-junctions. Furthermore, the screening arrangement comprises the ability to provide different, predefined bias currents Isc 19.

Solar cells to be screened are placed on a temperature controlled plate 30. There are no restrictions at which temperature the measurement is performed. A screening at room temperature is, however, most straight forward.

Figure 7:
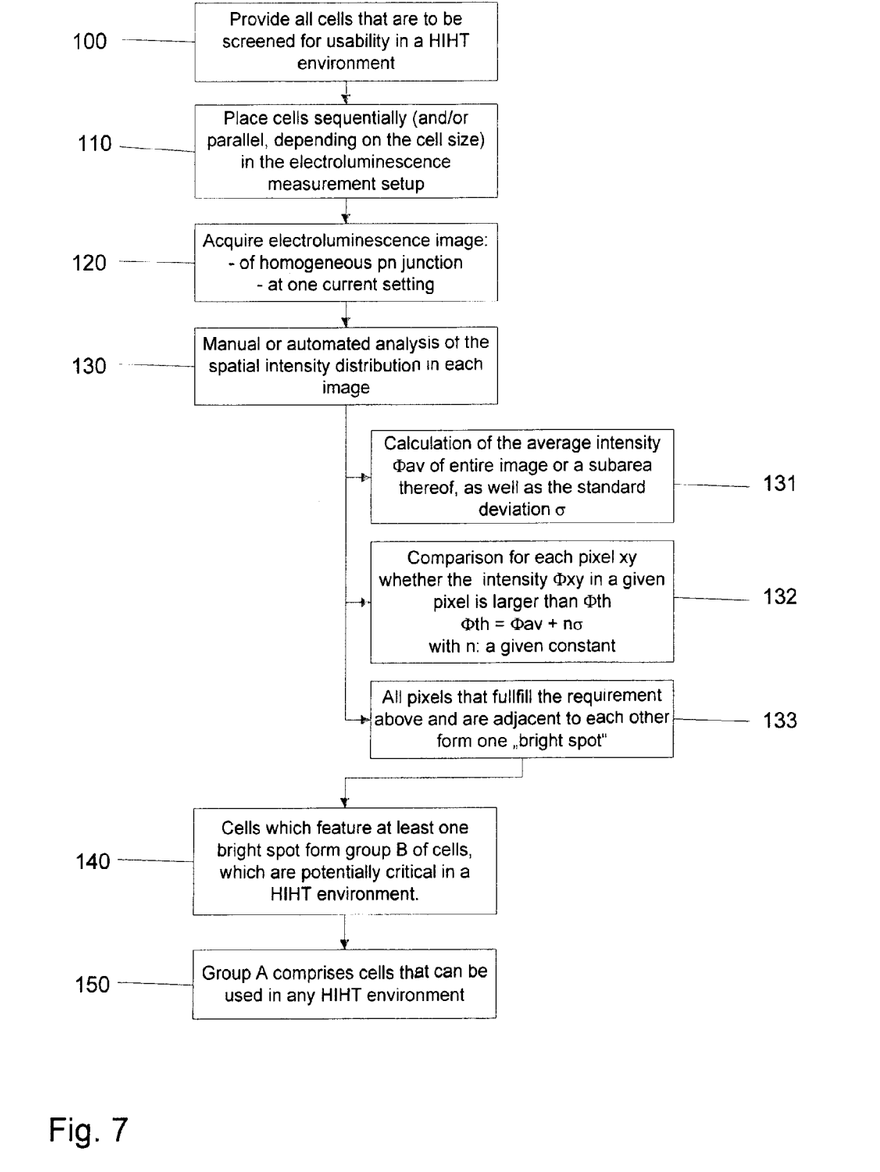
FIG. 7 shows a diagram illustrating the basic steps of the screening method according to the invention.
Figure 8:
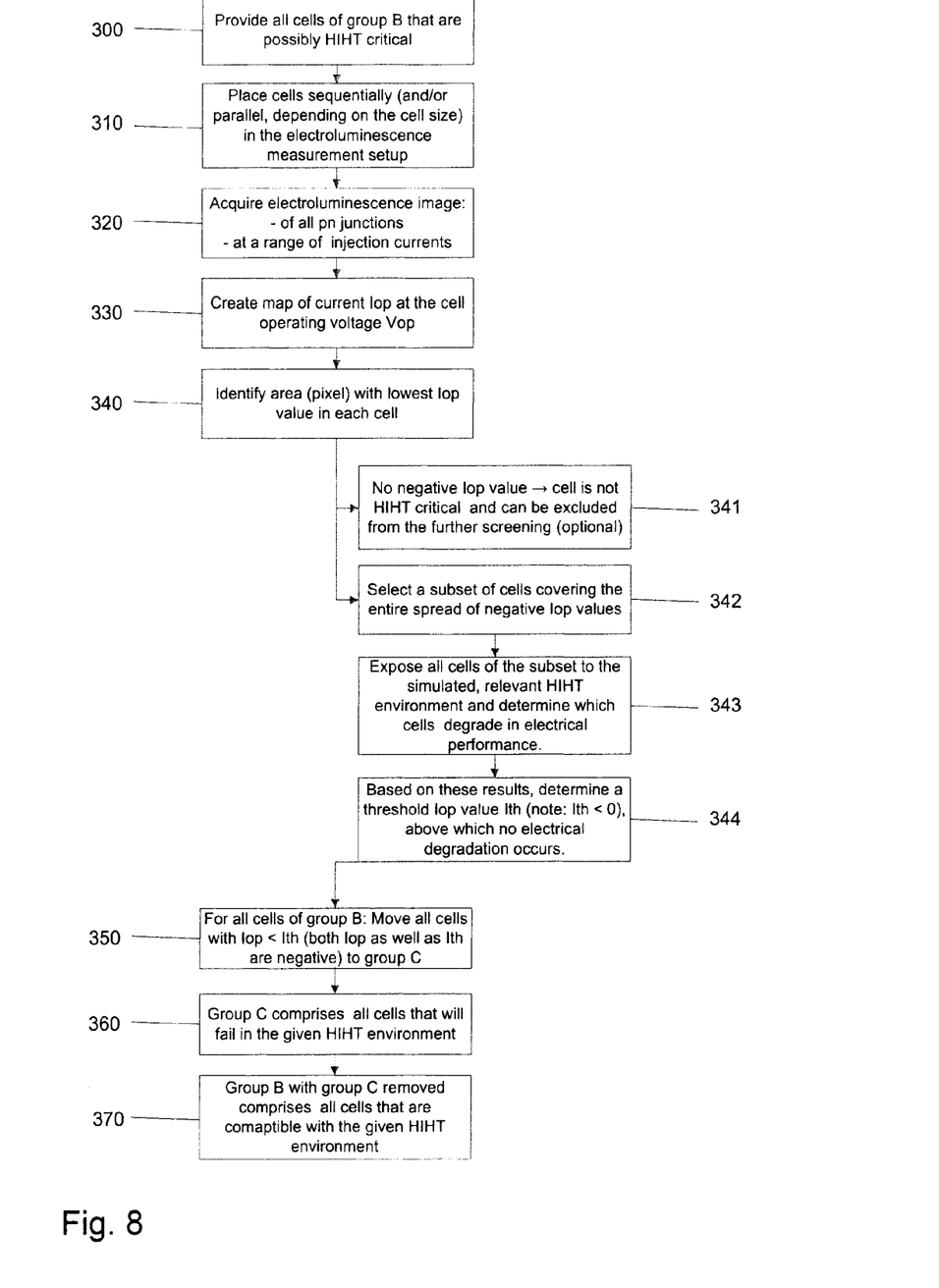
FIG. 8 shows a diagram illustrating optional steps of the screening process of the invention.

The screening method of the invention will be described in more detail by reference to FIGS. 7 and 8. FIG. 7 illustrates a diagram for a first, basic screening step. FIG. 8 illustrates the procedure for an optional second screening step. For carrying out the screening method according to the invention, it is necessary that the homogeneous pn-junction 6 of the solar cell is free of intrinsic defects such that its diode characteristics can be assumed to be homogeneous throughout. In addition this pn-junction has to emit detectable electroluminescence radiation under a forward bias.

At the beginning, (step 100) all cells that are to be screened for usability in a HIHT environment are provided. In step 110, they are placed on the temperature controlled plate 30. They can be placed sequentially and/or parallel (depending on the cell size and the capabilities of the detector 17) in the electroluminescence measurement setup shown in FIG. 6. Depending on the resolution of the detector 17, to record the electroluminescence image of each pn-junction separately, it might be feasible to screen several cells in parallel. Typical values of suitable detectors resolutions are around 2000 pixels/cm$^2$. The solar cell is connected to a power supply 9 and forward biased at a current Isc (cf. reference numeral 19). A practical choice for the current Isc is a current close to the short circuit current of the solar cell. Other settings are possible, the only requirement is that the solar cell emits sufficient electroluminescence radiation and is not damaged by excessive currents.

The electroluminescence is recorded in a spatially resolved manner (step 120) by the detector 17, i.e. a camera/CCD chip. The choice of the camera system is dictated by the fact that the camera has to have sufficient sensitivity in the spectral range of the emitted electroluminescence. For the Ge-subcell in the triple-junction cell shown in FIG. 6, an HgCdTe camera is most appropriate. In addition, a high dynamic resolution, ideally above 1:10000, is beneficial. A filter 15 or a set of filters is used to block the electroluminescence radiation emitted by all other pn-junctions 2, 3. Depending on the number of pn-junctions in the solar cell, a short path, a long path or a bandpass filter is required. In the example of a Ge-subcell, a 1550 nm long path filter is used. In addition, it might be beneficial if the entire measurement arrangement is within an enclosure that blocks all external light. This is illustrated with reference numeral 40 in FIG. 6.

According to step 130 the recorded image is automatically or manually analyzed by an image processing system on the computer 20. The average image intensity $\Phi_{av}$ of the entire solar cell or a subarea thereof is calculated (step 131) as well as the standard deviation $\sigma$. For each pixel xy in the image a comparison is made whether the intensity $\Phi_{xy}$ in this pixel is above a threshold value $\Phi_{th}$ given by $\Phi_{av}+n\sigma$ (step 132). In general, particularly for Ge-based triple-junction cells, n=6 is appropriate. All pixels that fulfill this requirement and are located adjacent to each other form one subassembly, called a "bright spot" which is a local intensity variation (step 133). Solar cells that feature at least one bright spot are put into a group B of cells which are potentially critical in a HIHT environment (140). The other cells are put into a group A. These solar cells are uncritical in any HIHT environment (step 150).

FIG. 8 illustrates the optional second screening step for those solar cells that are possibly critical in a HIHT environment. Therefore, only those solar cells of group B are screened further (step 300). The measurement setup employs additional detectors 10, 16 for all remaining pn-junctions as well as appropriate filters 11, 14. Depending on the spectral sensitivity of the detectors, the same detector might be used for different pn-junctions as long as the emission of any given pn-junction is isolated by an appropriate choice of filters that blocks the emission of all remaining junctions. The solar cell might be in the field of view of all detectors 10, 16, 17 or moved from one detector to the next. The detectors 10, 16 have to have a high dynamic resolution, e.g. above 1:10000. For a triple-junction cell with GaAs as middle cell 2 and GaInP$_2$ as top cell 3, a 700 nm cut off short path and an 800 nm long path filter together with a 16 bit Si CCD camera are used.

The computer 50 is used to automatically forward bias the cells at a range of currents 18, i.e. $I_1, I_2, \ldots, I_N$, and to create a spatial distribution map of the current produced by the solar cell at a given operating voltage. The detailed procedure is outlined in the aforementioned Zimmermann article which is incorporated by reference.

According to step 310 the solar cells of group B are placed in the measurement system and images of all pn-junctions at a range of injection currents are acquired (step 320). A map of current Iop at a given operating voltage of the solar cell is calculated automatically or manually according to step 330. In each solar cell, the pixels xy (i.e. basic units of the Iop map) or adjacent pixels with lowest Iop value are identified (step 340). Solar cells where no negative Iop value exists can be excluded from the screening right away (step 341) since no current is dissipated and therefore these cells are not sensitive to HIHT environments. This assorting is an optional step.

A subset of solar cells, featuring a broad spread of negative Iop values, is selected (step 342) and exposed to the particular HIHT environment of concern (step 343). A threshold value Ith is determined from these cells characterized by the fact that below the threshold current Ith (with Ith<0) the cells degrade whereas above Ith they are not affected. After this threshold value has be determined, all remaining solar cells of group B are checked to determine if there are any pixels with Iop<Ith. This step can be performed automatically by the computer 50. These cells form group C (step 350), which will fail in the particular HIHT environment (step 360). All other cells of group B (group B') can be used in the given HIHT environment according to step 370.

It should be recognized that the methods described above can be implemented using a computer, and in particular a processor executing appropriate instructions loaded from a non-transitory computer-readable medium.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

LIST OF REFERENCE NUMERALS 1 wafer
2 pn-junction
3 pn-junction
4 front side metallization
5 rear side metallization
6 diffusion area
7 defect with negligible electrical impact
8 defect with electrical impact
9 power supply
10 detector
11 filter
12 junction voltage
13 xy-position
14 filter
15 filter
16 detector
17 detector
18 injection current
19 current Isc
20 computer
22 local intensity variation
23 image
30 temperature controlled plate
40 enclosure
50 computer

What is claimed is:

1. A method for screening of multi-junction solar cells to be operated in a high sun intensity and high temperature (HIHT) environment, each of the solar cells comprising at least two pn-junctions stacked on top of each other wherein one of the pn-junctions is a completely homogeneous pn-junction assumed to be free of intrinsic defects, the method comprising the steps of:
   receiving a number of solar cells to be screened for usability in the HIHT environment; for each solar cell of the number of solar cells,
      acquiring an electroluminescence image of the homogeneous pn-junction at a predefined bias current;
      analyzing a spatial intensity distribution in the electroluminescence image to determine whether there are local intensity variations that possibly dissipate power in the HIHT environment;
      sorting the solar cells of the number of solar cells, wherein solar cells having no local intensity variations in their electroluminescence image are put into a first group of solar cells and solar cells having at least one local intensity variation in their electroluminescence image are put into a second group of solar cells for further screening, wherein solar cells of the first group are suitable for a HIHT environment and solar cells of the second group are assumed to be potentially critical in a HIHT environment.

2. The method according to claim 1, wherein the step of analyzing the spatial intensity distribution in the electroluminescence image comprises the steps of
   calculating of an average intensity $\Phi_{av}$ of the entire electroluminescence image or a sub area thereof and a standard deviation $\sigma$
   comparing for each pixel (xy) of the electroluminescence image whether the intensity $\Phi_{xy}$ in a given pixel is larger than a threshold intensity $\Phi_{th}$, wherein $\Phi_{th}=\Phi_{av}+n\sigma$, with n being a predefined constant; and
   assigning those pixels (xy) with an intensity $\Phi_{xy}$ larger than a threshold intensity $\Phi_{th}$ and which are adjacent to each other to form a local intensity variation.

3. The method according to claim 2, wherein n=6 for a triple junction solar cell.

4. The method according to claim 1, wherein the step of analyzing the spatial intensity distribution in the electroluminescence image is executed by an image processing system.

5. The method according to claim 1, wherein the homogeneous pn-junction is a Germanium (Ge)-wafer, on which the further pn-junction is grown.

6. The method according to claim 1, wherein the solar cells are placed on a temperature controlled plate, that is heated to a predefined temperature, during the acquiring and analyzing steps.

7. The method according to claim 1, wherein the acquiring electroluminescence image is performed with a detector having a resolution of around 2000 pixel/cm$^2$ or having a dynamic resolution of above 1:10000.

8. The method according to claim 1, wherein a set of filters is used to block electroluminescence radiation emitted by pn-junctions, other than the homogenous pn-junction.

9. The method according to claim 1, wherein the predefined bias current is a forward current close to a short circuit current of the solar cell such that the solar cell emits sufficient electroluminescence radiation for the acquiring of the electroluminescence image of the homogeneous pn-junction of the solar cell and that it is not damaged by the bias current.

10. The method according to claim 1, wherein the method further comprises a step of screening of the solar cells of the second group of solar cells, the screening comprising the steps of:
   acquiring an electroluminescence image of all pn-junctions of a respective solar cell at a range of predefined bias currents;
   for each solar cell of the solar cells of the second group,
      creating a spatial current distribution map of the current the solar cell produces at a given cell operating voltage, and
      identifying pixels or a group of adjacent pixels with a lowest current value; and
      sorting the solar cells into a third group of solar cells that are not suitable for the HIHT environment based on a lowest current value.

11. The method according to claim 10, wherein the step of identifying pixels (xy) with a lowest current value comprises a step of determining whether the lowest current value is negative.

12. The method according to claim 11, wherein when the lowest current value is not negative the solar cell is sorted into a fourth group of solar cells that are suitable for the HIHT environment.

13. The method according to claim 11, wherein when the lowest current value is negative the method comprises the steps of:
   selecting a subset of solar cells covering an entire spread of negative current values;
   exposing all solar cells of the subset to a simulated HIHT environment;
   determining solar cells with degraded electrical performance;
   determining a negative threshold current above which no electrical degradation occurs; and
   sorting solar cells with an operating current smaller than a threshold into the third group and sorting solar cells with an operating current greater than the threshold into the fourth group.

* * * * *